(12) United States Patent
Oberholtzer et al.

(10) Patent No.: US 8,382,732 B2
(45) Date of Patent: Feb. 26, 2013

(54) OSTOMY APPLIANCE

(75) Inventors: Gary Oberholtzer, Skillman, NJ (US);
Kenneth Johnsen, Skillman, NJ (US)

(73) Assignee: ConvaTec Technologies Inc., Las Vegas, NV (US)

( * ) Notice: Subject to any disclaimer, the term of this patent is extended or adjusted under 35 U.S.C. 154(b) by 569 days.

(21) Appl. No.: 12/673,644

(22) PCT Filed: Aug. 18, 2008

(86) PCT No.: PCT/US2008/073496
§ 371 (c)(1),
(2), (4) Date: Feb. 16, 2010

(87) PCT Pub. No.: WO2009/023871
PCT Pub. Date: Feb. 19, 2009

(65) Prior Publication Data
US 2011/0178483 A1 Jul. 21, 2011

Related U.S. Application Data

(60) Provisional application No. 60/956,238, filed on Aug. 16, 2007.

(51) Int. Cl.
*A61F 5/44* (2006.01)

(52) U.S. Cl. ........ 604/344; 604/342; 604/338; 604/332; 604/341; 604/343; 604/336

(58) Field of Classification Search ............. 604/344, 604/342, 338, 332, 339, 341, 343, 336
See application file for complete search history.

(56) References Cited

U.S. PATENT DOCUMENTS

| 4,419,100 A | 12/1983 | Alexander |
| 4,610,676 A | 9/1986 | Schneider et al. |
| 4,610,677 A | 9/1986 | Mohiuddin |
| 4,950,223 A | 8/1990 | Silvanov |
| 5,312,382 A | 5/1994 | Metz |
| 5,730,735 A | 3/1998 | Holmberg et al. |
| 2007/0088300 A1 | 4/2007 | Cline |

FOREIGN PATENT DOCUMENTS

| WO | WO2005070356 A1 | 8/2005 |
| WO | WO2009/023870 | 2/2009 |

*Primary Examiner* — Tatyana Zalukaeva
*Assistant Examiner* — Ginger T Chapman
(74) *Attorney, Agent, or Firm* — Stuart E. Krieger

(57) ABSTRACT

An ostomy coupling is disclosed comprising a floatable coupling part. The coupling part is supported with respect to an adhesive wafer by means of a flexible support collar that permits displacement of the coupling part in a floatable manner. The flexible collar comprises plastics film and has bistable shapes. The collar is configured to hold the coupling part stably in (i) an extended position spaced from the adhesive wafer, to facilitate an ostomate to manually brace the coupling part in order to relieve the attachment force when an ostomy appliance is press fitted to the coupling part, and (ii) in a retracted position close to the adhesive wafer.

20 Claims, 6 Drawing Sheets

OSTOMY APPLIANCE

FIELD OF THE INVENTION

The present invention relates to an ostomy coupling for removably attaching an ostomy appliance to a body fitment worn on the body of an ostomate. In one form, the invention relates to providing a body fitment with a floatable coupling part.

BACKGROUND TO THE INVENTION

U.S. Pat. No. 4,419,100, U.S. Pat. No. 4,610,676, U.S. Pat. No. 4,610,677, U.S. Pat. No. 5,730,735 and U.S. Pat. No. 5,312,382 teach an ostomy coupling designed to reduce discomfort that some ostomates experience as a result of an attachment force applied through the body fitment to the skin, when two coupling parts are pressed together. The problem of discomfort is especially important during post-operative care, when the stoma surgery is recent and the abdominal skin is very tender. These documents teach a flexible collar suspension permanently secured between the adhesive wafer and the coupling part of the body fitment. The flexible collar allows the coupling part to be displaced away from or "float" with respect to the adhesive wafer, at least by a sufficient amount for a user to insert one or more fingers behind the coupling part, in order to manually support the coupling part against the attachment force when the appliance is pressed against the body fitment. Such a coupling part is generally referred to in the art as being a floating coupling part.

While this technique is successful in reducing transmission of the attachment force to the sensitive abdominal skin during post-operative care, there are several disadvantages that make this type of coupling less than ideal for everyday use. These include: (1) the profile of the system is higher than similar systems without a flexible collar, due to the increased thickness; and (2) there is a tendency for the appliance to sag away from the adhesive wafer, since the flexible collar is explicitly provided to allow the pouch to float away from the surface of the wafer. It is possible to increase the stiffness of the flexible collar, in order to reduce such sagging and maintain a low profile, but the stiffer the collar, the greater is the force that the ostomate has to apply to displace the coupling part away from the adhesive wafer, and to maintain the coupling part in the displaced position. This can be inconvenient for the ostomate, especially elderly or less dexterous ostomates. More importantly, at least some of the increased force applied to the coupling part when pulling and maintaining it away from the wafer, will inevitably be transmitted to the underlying tender skin, risking increasing the amount of discomfort instead of reducing discomfort. These problems of the prior art designs cannot easily be resolved to increase ostomate approval of the floating coupling part idea, because the problems are a result of two intractably conflicting desiderata of the floating coupling part.

The present invention has been devised bearing the above in mind.

SUMMARY OF THE INVENTION

In one aspect, the present invention provides an ostomy coupling comprising a floatable coupling part. The coupling part is supported with respect to an adhesive wafer by means of a flexible support collar that permits displacement of the coupling part in a floatable manner. The flexible collar comprises plastics film and has bistable shapes. The collar is configured to hold the coupling part stably in (i) an extended position spaced from the adhesive wafer, to facilitate an ostomate to manually brace the coupling part in order to relieve the attachment force when an ostomy appliance is press fitted to the coupling part, and (ii) in a retracted position close to the adhesive wafer.

The use of such bistable support can solve the conflicting desiderata of the prior art. In the retracted position, the support can hold the coupling part close to the adhesive wafer, to resist sagging and maintain a low profile height. In the extended position, the support can hold the coupling part spaced from the adhesive wafer, without any pulling force required to be maintained that may be uncomfortable to the underlying skin. The flexible support collar may be formed of plastics film, and so be economical to produce without substantially increasing the cost of the ostomy apparatus.

In another aspect, the invention generally provides a bistable support for a coupling part of an ostomy coupling, the bistable support having a through passage and first and second interface regions. The first interface region is connected to the coupling part. The second interface region is secured or is securable, directly or indirectly, to an adhesive wafer. The bistable support is configured to hold the coupling part stably in (i) an extended position in which the first and second interface regions are substantially spaced apart in an axial direction of the through passage, and (ii) in a retracted position in which the first and second interface regions are positioned closer together in the axial direction. The bistable support may optionally comprise a flexible collar. The first and second interface regions may optionally comprise, one or the other of, inner and outer peripheries of the flexible collar.

As used herein, the term "releasably attaching" and derivatives thereof mean that two coupling parts are attachable and detachable, using forces applied by hand, and without destruction of either part. The term "floatable" means that a coupling part is movable towards and away from an adhesive wafer, to create a space for a user to manually brace that coupling part, in order to relieve attachment forces being applied through the adhesive wafer.

While features believed to be most important are highlighted above, in description, and in the appended claims, the Applicants may seek claims protection for any novel feature or idea disclosed herein and/or in the drawings, whether or not emphasis has been placed thereon.

DETAILED DESCRIPTION OF PREFERRED EMBODIMENTS

Figure 1:
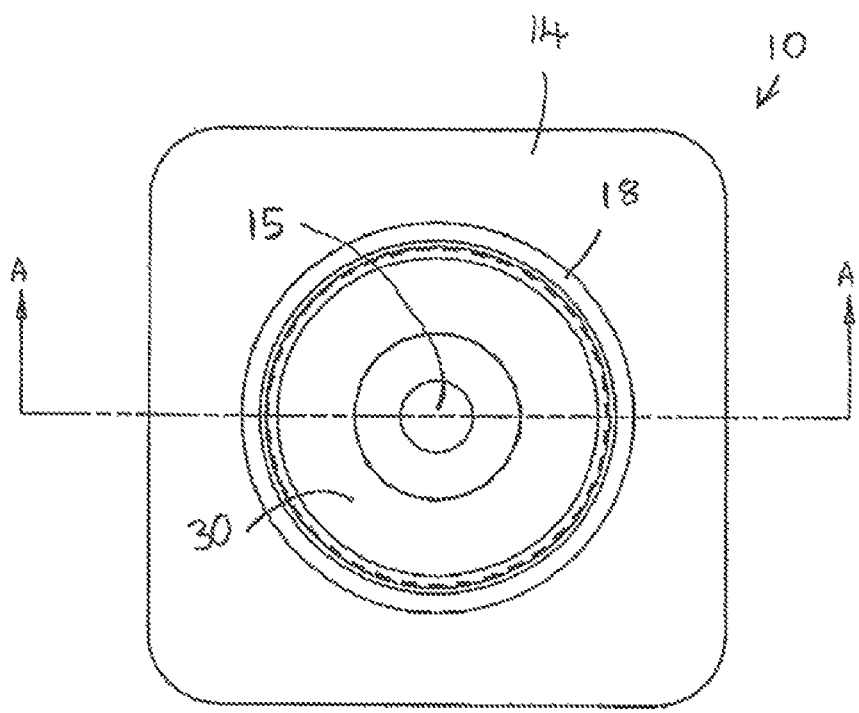
FIG. 1 is a schematic plan view of a first embodiment of the invention in an ostomy body fitment.
Figure 2:
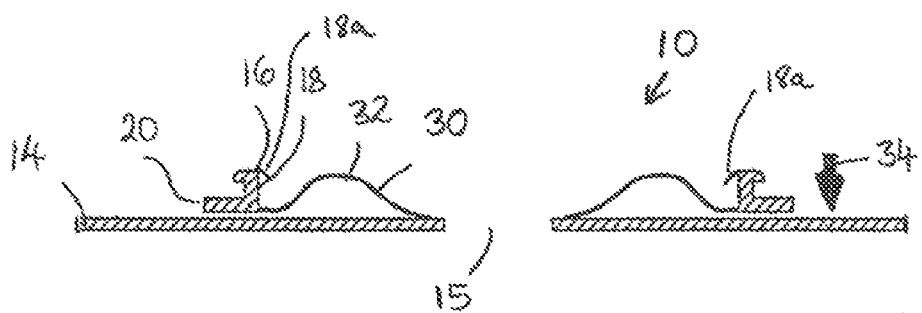
FIG. 2 is a schematic sectional view along the line A-A of FIG. 1, and showing the coupling part retracted.

Preferred embodiments of the invention are now described with reference to the accompanying drawings. The same reference numerals are used to denote the same or equivalent features in each embodiment.

Referring to FIGS. 1 to 4, ostomy apparatus generally comprises a body fitment 10 (FIGS. 1-3) and an ostomy appliance 12 (FIG. 4) in the form of a collection pouch 26. The body fitment 10 comprises an adhesive wafer 14 with a stomal orifice 15, for attachment to the ostomate's skin. The adhesive wafer 14 may comprise any suitable skin-friendly ostomy adhesive, such as a hydrocolloid containing adhesive. A suitable adhesive is that marketed under the brand Stomahesive by ConvaTec, a division of E.R. Squibb & Sons, L.L.C. The body fitment 10 further comprises a body-side coupling part 16 that is secured to the adhesive wafer 14 around the stomal orifice 15 by means of a flexible support collar 30. The body-side coupling part 16 is configured to releasably attachably engage a complementary appliance-side coupling part 22 secured to the collection pouch 26 around an entrance aperture 28. In the present embodiment, the coupling parts 16, 22 form a mechanical engagement (for example, a mechanical interlock or an interference fit). The body-side body coupling part 16 comprises a flange 20 from which projects an upstanding rib 18, with an undercut lug 18a. The appliance-side coupling part 22 comprises a channel for receiving the upstanding rib 18. The channel has a complementary lug (not shown) for interlocking with the undercut lug 18a of the body-side coupling part 16, when the upstanding rib 18 is received in the channel. An optional grip tab 24 projects from the channel to aid manipulation of the ostomy appliance 12. The two coupling parts 16, 22 are made from molded plastics that are stiffly flexible with a self-supporting shape. The flexible support collar 30 includes an outer periphery as a first interface region attached to the body-side coupling part 16, and an inner periphery as a second interface region attached, directly or indirectly, the adhesive wafer 14.

The flexible support collar 30 permits the body-side coupling part 16 to move with respect to the adhesive wafer 14 between a retracted position (FIG. 2) in which the body-side coupling part 16 fits generally close to or against the adhesive wafer 14, and an extended position (FIG. 3) in which the body-side coupling part 16 is spaced away from the adhesive wafer 14. In this embodiment, the flexible support collar 30 holds the body-side coupling part 16 stably in the retracted position as a first stable position and in the extended position as a second stable position. The flexible support collar 30 may be regarded as giving the body-side coupling part 16 a "floatable" characteristic in the sense that the body-side coupling part 16 is displaceable away from the adhesive wafer 14. The flexible support collar 30 and the body-side coupling part 16 may together be referred to as a floatable coupling unit. However, the body-side coupling part 16 is not "floating" in the sense of the prior art, because the body-side coupling part 16 is held by the flexible support collar 30 in bistable positions, rather than floating freely or being biased only to the retracted position.

In the extended position, the flexible support collar 30 has a three-dimensional flared shape, which can be inherently self supporting. The flared shape may, for example, be substantially conical (substantially frusto-conical). The flexible support collar 30 may optionally be formed (e.g., thermoformed from sheet material, or molded) in this shape as a natural shape, or the flexible support collar 30 may be formed in a different shape and hold itself stably in the flared shape by internal stress in the material. In the extended position, the inner and outer peripheries of the flexible support collar 30 are substantially spaced from each other along the axis of the through passage through the flexible support collar 30.

In the retracted position, the flexible support collar 30 has a corrugated or rippled shape, with at least one corrugation or ripple pleat 32. The retracted position may itself be a stable position of the flexible support collar 30, or the flexible support collar 30 may be biased towards an even further retracted position, but prevented from reaching that position by the flexible support collar 30 and/or the body-side coupling part 16 bearing against the adhesive wafer 14 as a stop. The flexible support collar 30 may be formed (e.g., molded or thermoformed) in the retracted shape, or it may hold itself stably in this shape by internal stress in the material. In the retracted position, the inner and outer peripheries of the flexible support collar 30 are closer together, viewed in an axial direction, than in the extended position.

The flexible support collar 30 may be bistable, having only two stable shapes, or it may have other stable shapes. The flexible support collar 30 may be flipped between the retracted and extended shapes by manual finger pressure applied, for example, by the ostomate. The corrugation or ripple pleat 32 overcenters to accommodate the flipping movement between the stable shapes. The height or prominence of the corrugation or ripple pleat 32 may be one of the geometric factors that determines the relative stability of the material in the two stable positions.

Figure 3:
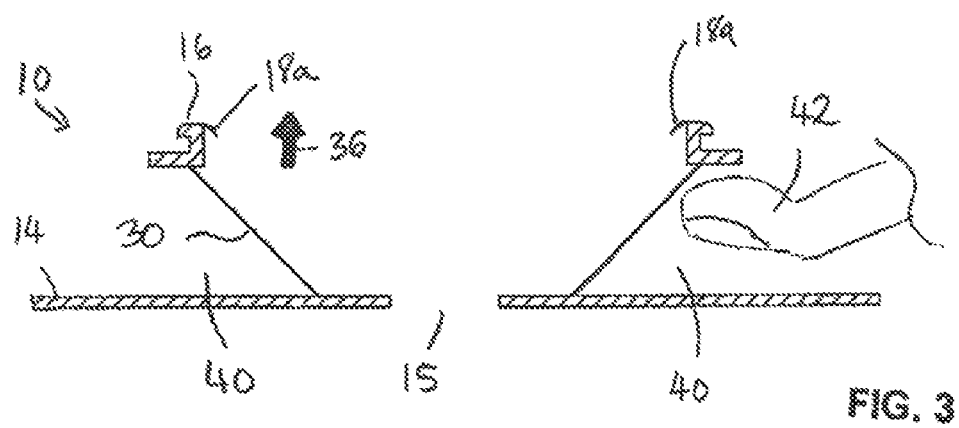
FIG. 3 is a schematic sectional view along the line A-A of FIG. 1, and showing the coupling part extended.
Figure 4:
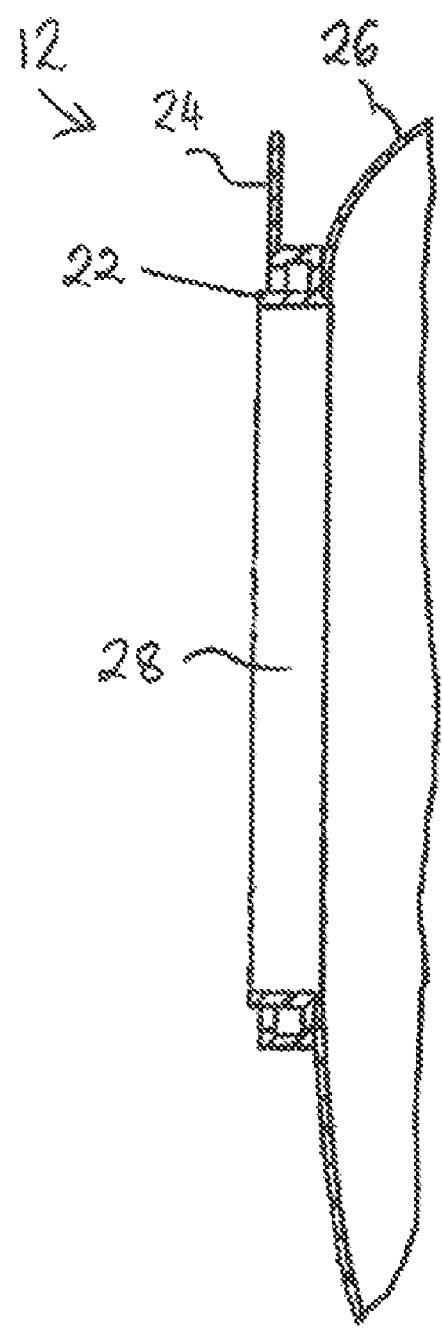
FIG. 4 is a schematic sectional view through an ostomy pouch appliance attachable to the body-fitment of FIG. 1.

In use, when the body fitment 10 is worn on the body, and the ostomate desires to attach an ostomy appliance 12, the ostomate first pulls the body-side coupling part 16 forward (arrow 36 in FIG. 3). The flexible support collar 30 flips to its extended shape, providing an annular space 40 between the body-side coupling part 16 and the adhesive wafer 14 for the user to insert one or more fingers 42 of one or both hands. Although the user does have to apply some force for a very short period of time to displace the body-side coupling part 16, once in the extended configuration the user does not have to maintain any pulling force on the body-side coupling part 16, and so the underlying skin is relieved of such uncomfortable force while the body-side coupling part 16 remains in its displaced, extended position. This is a major advantage.

To fit the ostomy appliance 12, the user then presses the appliance-side coupling part 22 into engagement with the body-side coupling part 16, while at the same time using his fingers 42 to brace the body-side coupling part 16, in order to relieve the attachment force from being transmitted through the body fitment 10 to the ostomate's skin.

Once the ostomy appliance 12 has been fitted, the user removes his fingers 42 from the annular space 40, and then gently pushes the ostomy appliance 12 towards the body fitment 10. This pushing action flips the flexible support collar 30 to its retracted shape, pulling the body-side coupling part 16 into a close fit against the adhesive wafer 14 (illustrated by the arrow 34 of FIG. 2). The stable shape of the flexible support collar 30 in its retracted position resists sagging of the ostomy appliance 12 away from the adhesive wafer 14. The body fitment 10 may therefore be conveniently used for post-operative care and for everyday use.

The flexible support collar 30 is made of any suitable material that can provide the desired stable shapes, with the desired stability of each shape. For example, the flexible support collar 30 may be made of plastic film. The plastic film may be resiliently stretchable, or it may be substantially non-stretchable. Suitable films include, for example, ethylene vinyl acetate copolymer (EVA), polyethylene (PE) or metalocene film, with a thickness of between 0.002 in. and 0.020 in. The flexible support collar 30 is attached to the body-side coupling part 16 and to the adhesive wafer 14 (or to a backing thereof) by any suitable technique, such as welding or adhesive bonding. Alternatively, the flexible support collar 30 could be integrally formed (e.g., molded) with another component of the body fitment 10, such as the body-side coupling part 16.

Figure 5:
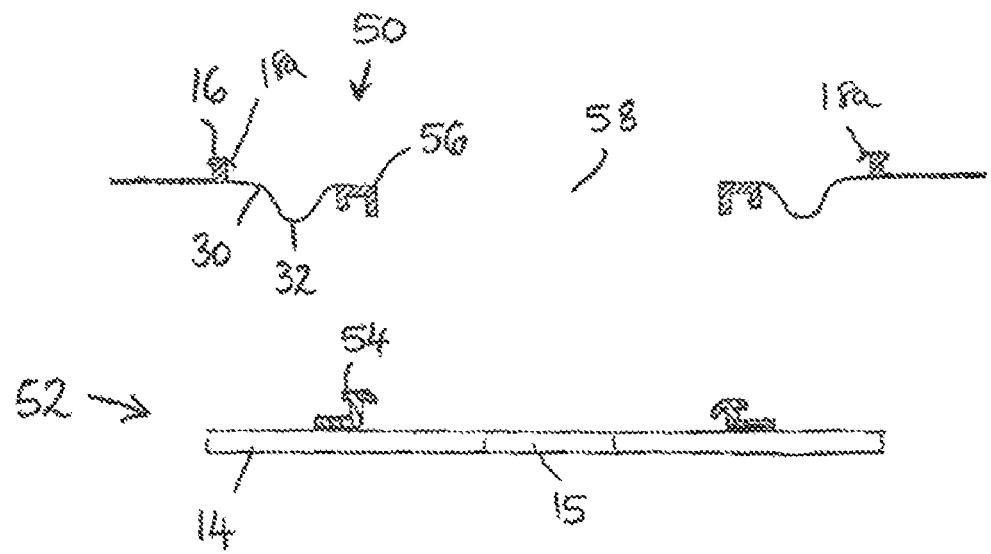
FIG. 5 is a schematic sectional view through a second embodiment of the invention in the form of an ostomy coupling adapter, and showing the coupling part retracted.
Figure 6:
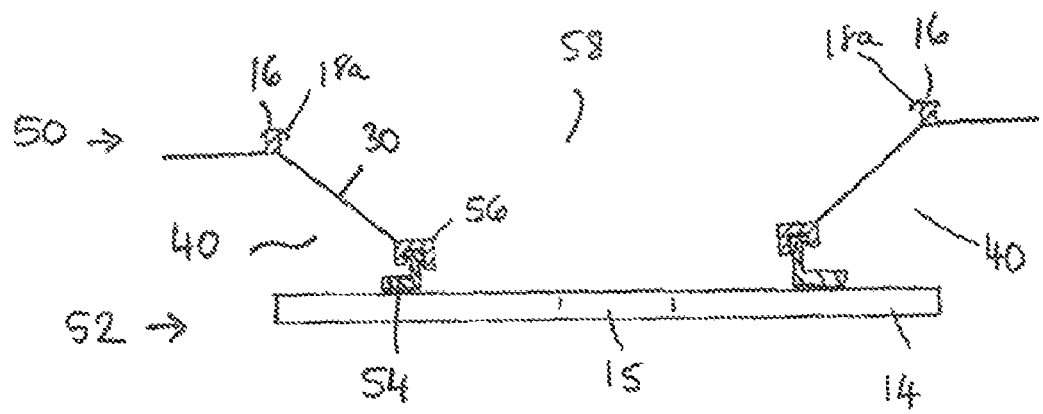
FIG. 6 is a schematic sectional view through the second embodiment attached to a body fitment, and showing the coupling part extended.

FIGS. 5 and 6 illustrate a second embodiment in the form of an adapter 50 for fitting between a body fitment 52 and the ostomy appliance 12. In this embodiment, the body fitment 52 differs from the body fitment 10 previously described, by having a non-floatable body-side coupling part 54. At least a portion of the body-side coupling part 54 is substantially fixed in position relative to the adhesive wafer 14. The adapter 50 provides the body fitment 52 with a floatable coupling characteristic, to increase the versatility of the body fitment 52.

The adapter 50 comprises the flexible support collar 30 previously described, a first coupling part 56 for attachment to the body-side coupling part 54, and a body-side coupling part 16 for releasable attachment to the ostomy appliance 12. The flexible support collar 30 has a first stable retracted position (FIG. 5) and a second stable extended position (FIG. 6). The flexible support collar 30 may include any of the features previously described.

Figure 7:
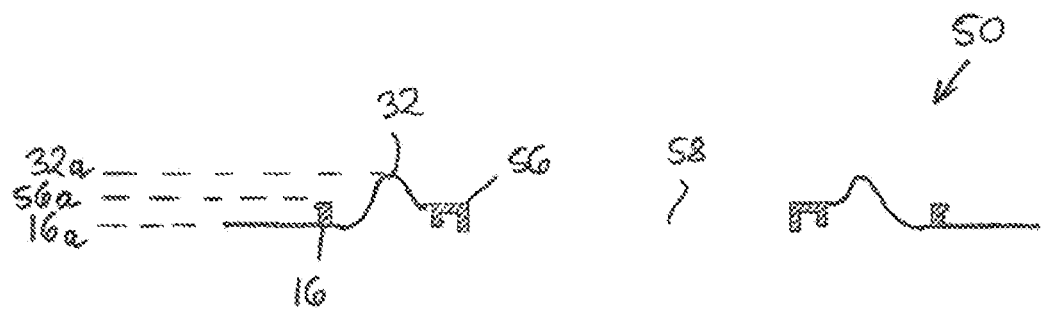
FIG. 7 is a schematic sectional view through a third embodiment of the invention in the form of an ostomy coupling adapter, and showing the coupling part retracted.
Figure 8:
FIG. 8 is a schematic sectional view through the third embodiment, showing the coupling part extended.

FIGS. 7 and 8 illustrate a third embodiment in the form of an adapter 50, similar to the second embodiment. The main difference is that, in the third embodiment, the corrugation or ripple pleat 32 projects towards the appliance-side (FIG. 7), instead of towards the body fitment side as in the second embodiment (FIG. 5). The shape of the third embodiment may enable one or more of the following: (i) the ripple pleat 32 can have a relatively high height 32a compared to the levels 16a, 56a of the coupling parts 16, 56. A greater height may provide additional stability of the extended and retracted shapes, and may also allow a greater throw length of the flexible support collar 30 when in the extended shape; and/or (ii) the body-side coupling part 16 may overlap the first coupling part 56 in an axial direction, such that the rear of the body-sided coupling part 16, when in the retracted position, sits behind the level of the front 56a of the first coupling part 56. This can provide an adapter 50 with an extremely low profile. When the adapter 50 of the third embodiment is coupled to the body fitment 52, the assembly may have substantially the same profile height or thickness as the body fitment 52 itself.

Figure 9:
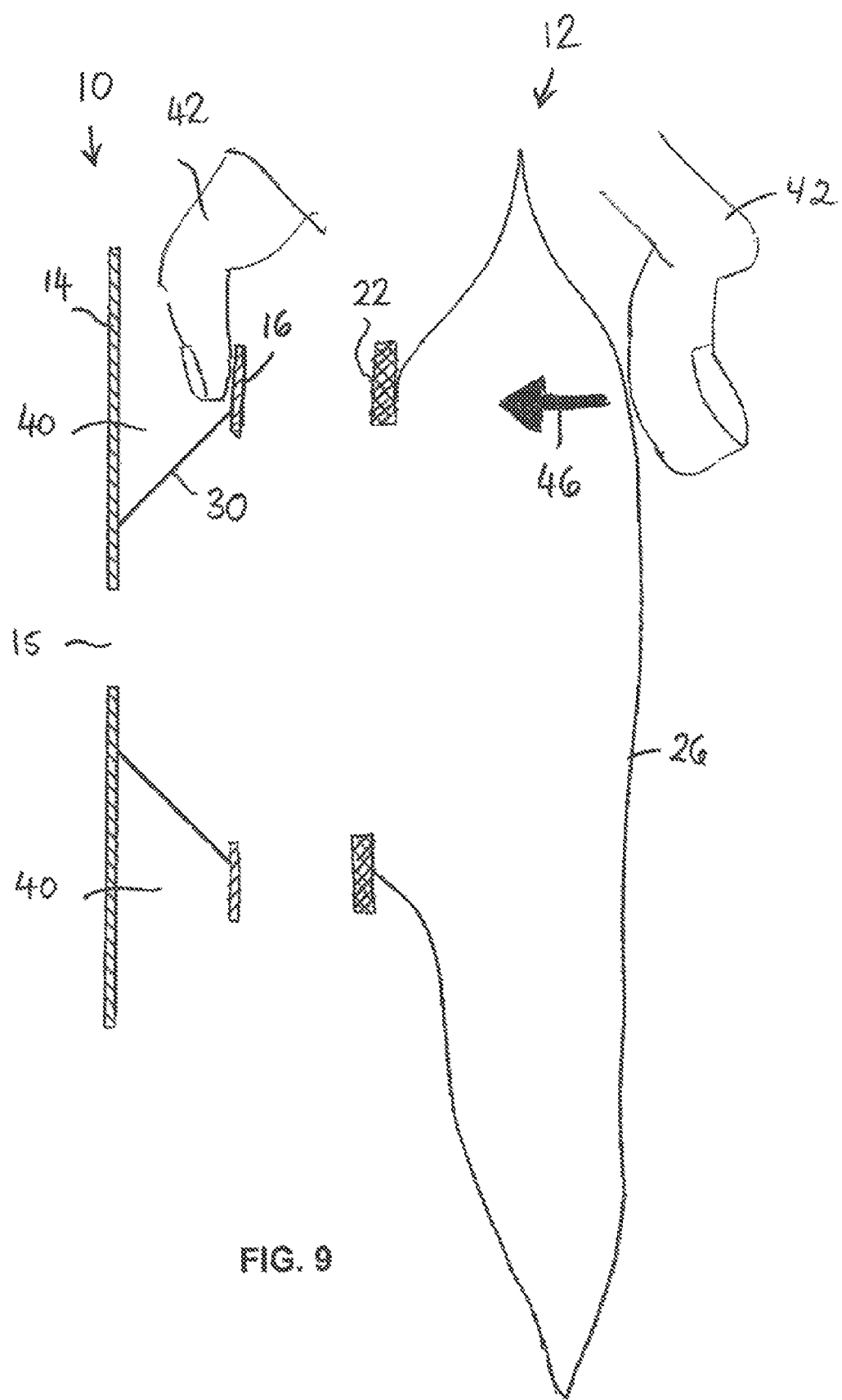
FIG. 9 is a schematic sectional view through a fourth embodiment of the invention.

FIG. 9 illustrates a fourth embodiment of the invention, similar to the first embodiment. The main difference is that, in the fourth embodiment, the body-side coupling part 16 and the appliance-side coupling part 22 are adhesively attachable instead of mechanically attachable. At least one of the coupling parts 16, 22 may carry a peelable-resealable adhesive, such as an acrylate-based peelable-resealable adhesive. The other of the coupling parts 16, 22 may also carry an adhesive, or it may comprise a generally non-adhesive landing surface for adhesive engagement. The fourth embodiment includes the same flexible support collar 30 for holding the body-side coupling part 16 stably in a retracted shape (not shown) and an extended shape (FIG. 9).

The preceding embodiments illustrate a flexible support collar 30 that has generally different diameters at respective inner and outer peripheries, and adopts a flared shape when extended. For example, in the case of the second and third embodiments, this enables the adapter 50 to join an ostomy appliance 12 to a body fitment 52 that has a different diameter of coupling part from the ostomy appliance 12. The diameters of the body-side coupling part 16 of the adapter 50, and of the body-side coupling part 54 of the body fitment 52, can be different.

Figure 10:
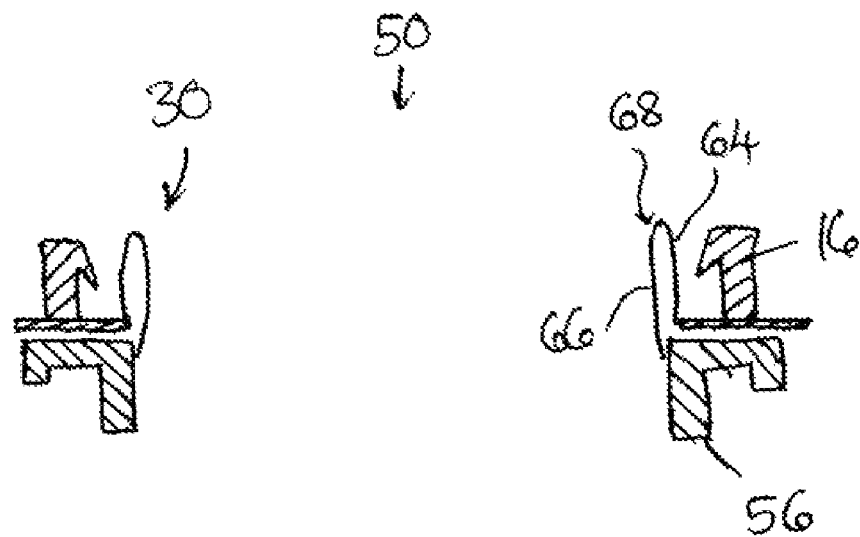
FIG. 10 is a schematic sectional view through a fifth embodiment in the form of an ostomy coupling adapter, and showing the coupling part retracted.
Figure 11:
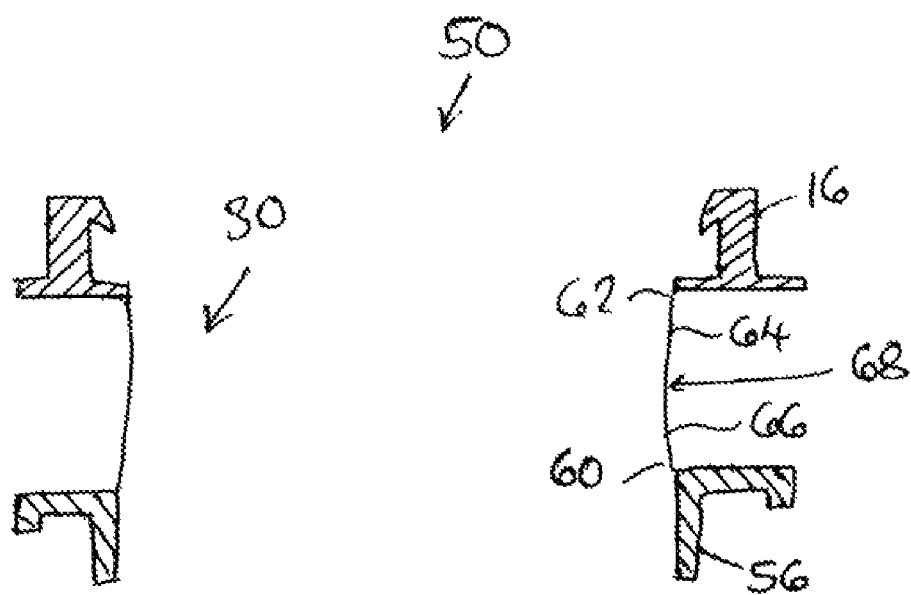
FIG. 11 is a schematic sectional view through the fifth embodiment, and showing the coupling part extended.

FIGS. 10 and 11 illustrate a fifth embodiment similar to the second and third embodiments except that, in the fifth embodiment, the flexible support collar 30 extends between portions of substantially the same diameter. The flexible support collar 30 comprises a first end 60 secured to the first coupling part 56, and a second end 62 secured to the body-side coupling part 16. The first and second ends 60, 62 are of substantially the same diameter, thereby enabling the adapter 50 to fit between a body fitment 52 and an ostomy appliance 12 having coupling parts of matching size. This is advantageous by providing fully compliant modularity, using existing ostomy components of matching size. A user can choose selectively whether to attach the ostomy appliance 12 directly to the body fitment 52, or whether to employ the adapter 50 (for example, if the stoma is particularly sensitive for any reason).

The flexible support collar 30 of the fifth embodiment can take a variety of forms. In one form as illustrated, the flexible support collar 30 is generally tubular, forming an extended tube when in the extended condition (FIG. 11), and a folded tube when in the retracted condition (FIG. 10). The flexible support collar 30 may comprise tubular segments 64, 66 that meet at a fold point 68, so that one segment may invert to nest within the other in the retracted condition. The flexibility of the material, and the fold point 68, may allow overcentering movement between the two stable positions. The flexible support collar 30 may be molded in one condition (such as the retracted condition), and be stable in the other condition by virtue of stresses in the material. Also, as explained previously, the flexible support collar 30 may be molded in a different shape to bias the shape of the support.

The flexible support collar 30 is shaped so that, in the retracted position, the flexible support collar 30 does not substantially obstruct back-to-back positioning of the coupling parts 16, 56 of the adapter 50 (see FIG. 10). For example, the tubular segments 64, 66 are received substantially within the aperture(s) of one or both coupling parts 16, 56. This permits the adapter 50 to adopt a low-profile shape in the retracted condition, so as limit the extent to which the adapter 50 adds to the profile of the ostomy appliance 12 and the body fitment 52 in use. It will be appreciated that the ends of the tubular flexible support collar 30 may be attached to the back-to-back faces of the coupling parts 16, 56, but this does not significantly space the coupling parts 16, 56 from each other in the retracted position.

The tubular-shaped flexible support collar 30 of the fifth embodiment may also be incorporated into any of the other embodiments, should it be desired not to employ a flared-shape flexible support collar 30.

Although not illustrated, adhesive coupling parts could also be used in the adapter 50 of the second and third embodiments, in place of the illustrated mechanical engagement coupling parts 16, 56. Also, although not illustrated, the invention is not limited to a flexible support collar 30. An equivalent supporting function may also be achieved by other non-collar shaped bistable supports.

It will be appreciated that many modifications, improvements and equivalents may fall within the scope of the invention as claimed.

We claim:

1. A floatable coupling unit for an ostomy coupling for releasably attaching an ostomy appliance to a body fitment, the floatable coupling unit comprising:
    a coupling part for releasable attachment to a complementary appliance-side coupling part; and
    a flexible support collar extending from the coupling part for supporting the coupling part, the flexible support collar permitting floatable displacement of the coupling part, and being configured to hold the coupling part stably in (i) an extended position and (ii) a retracted position; by means of internal stress in the material of the flexible support collar.

2. The floatable coupling unit of claim 1, wherein the flexible support collar is configured to have a flared shape when in the extended position.

3. The floatable coupling unit of claim 2, wherein the flared shape is substantially frusto-conical.

4. The floatable coupling unit of claim 1, wherein the flexible support collar is configured to have a corrugated shape when in the retracted position, the corrugated shape comprising at least one corrugation pleat.

5. The floating coupling unit of claim 1, wherein the flexible support collar has ends of substantially the same diameter.

6. The floating coupling unit of claim 1, wherein the flexible support collar has a configuration selected as one of more of: (i) an extended tube when in the extended position, (ii) a folded tube when in the retracted position.

7. The floatable coupling unit of claim 1, wherein the flexible support collar is formed in a predetermined shape as a natural shape of the flexible support collar, the predetermined shape being one of the shapes for the extended position and the retracted position.

8. The floatable coupling unit of claim 1, wherein the flexible support collar has bistable shapes.

9. The floating coupling unit of claim 1, wherein the flexible support collar is formed of plastics film.

10. The floating coupling unit of claim 9 wherein the plastics film is selected from the group consisting of ethylene vinyl acetate copolymer (EVA), polyethylene (PE) or metalocene.

11. The floating coupling unit of claim 9, wherein the plastics film has a thickness of between about 0.002 in. and 0.020 in.

12. The floating coupling unit of claim 1, wherein the flexible support collar is configured to flip between the stable shapes when a predetermined force is applied.

13. An ostomy coupling comprising:
    an appliance-side coupling part having an orifice therethrough;
    a body-fitment-side coupling part having an orifice therethrough; and
    a flexible support collar extending from the body-fitment-side coupling part for supporting the body-fitment-side coupling part, the flexible support collar permitting displacement of the body-fitment-side coupling part, and being configured to hold the body-fitment-side coupling part stably in (i) an extended position for permitting a user manually to brace the body-fitment-side coupling part to relieve an attachment force when the coupling parts are pressed into engagement, and (ii) in a retracted position; by means of internal stress in the material of the flexible support collar.

14. The ostomy coupling of claim 13, wherein the coupling parts are releasably attachable together by mechanical engagement, or by adhesive engagement.

15. An ostomy body fitment for releasably mounting an ostomy appliance, the body fitment comprising:
    an adhesive wafer for adhesive attachment to skin;
    a coupling part for releasably attaching to a complementary coupling part of an ostomy appliance; and
    a flexible support collar for supporting the coupling part with respect to the adhesive wafer, the flexible support collar extending from the coupling part and being joined directly or indirectly to the adhesive wafer, the flexible support collar permitting floatable displacement of the coupling part with respect to the adhesive wafer, and being configured to hold the coupling part stably in (i) an extended position and (ii) a retracted position; by means of internal stress in the material of the flexible support collar.

16. The ostomy body fitment according to claim 15, wherein, in the retracted position, the flexible support collar holds the coupling part to bear directly or indirectly against the adhesive wafer.

17. A method of supporting a coupling part in a floatable manner with respect to an adhesive wafer of an ostomy body fitment, the method comprising:
    providing a flexible support collar between the adhesive wafer and the coupling part, the flexible support collar permitting floatable displacement of the coupling part with respect to the adhesive wafer, and being configured to hold the coupling part stably in (i) an extended position and (ii) a retracted position; by means of internal stress in the material of the flexible support collar.

18. A bistable support for a coupling part of an ostomy coupling, the bistable support having a through passage and first and second interface regions, the first interface region being connected to the coupling part, and the second interface region being secured or securable, directly or indirectly, to an adhesive wafer, the bistable support being configured to hold the coupling part stably in (i) an extended position in which the first and second interface regions are substantially spaced apart in an axial direction of the through passage, and (ii) in a retracted position; by means of internal stress in the material of the flexible support collar in which the first and second interface regions are positioned closer together in the axial direction.

19. The bistable support of claim 18, wherein the bistable support comprises a flexible support collar.

20. The bistable support of claim 19, wherein the first and second interface regions are selected from the group consisting of (i) one or the other of, inner and outer peripheries of the flexible collar; and (ii) opposite ends of a tubular flexible collar.

* * * * *